United States Patent [19]

Blesener et al.

[11] Patent Number: 5,262,841
[45] Date of Patent: Nov. 16, 1993

[54] VACUUM PARTICLE DETECTOR

[75] Inventors: James L. Blesener, White Bear Lake; Thomas G. Halvorsen, Blaine, both of Minn.

[73] Assignee: TSI Incorporated, St. Paul, Minn.

[21] Appl. No.: 777,016

[22] Filed: Oct. 16, 1991

[51] Int. Cl.$^5$ ............................................. G01N 21/00
[52] U.S. Cl. .................................. 356/338; 356/336; 250/574
[58] Field of Search ............................. 356/335-343; 250/222.2, 574

[56] References Cited

U.S. PATENT DOCUMENTS

| | | |
|---|---|---|
| 3,614,231 | 10/1971 | Shaw . |
| 3,630,617 | 12/1971 | Marrett ............................ 250/574 |
| 3,646,352 | 2/1972 | Bol et al. ......................... 356/336 |
| 3,713,743 | 1/1973 | Simms ............................. 356/338 |
| 3,770,351 | 11/1973 | Wyatt . |
| 4,178,103 | 12/1979 | Wallace . |
| 4,761,074 | 8/1988 | Kohsaka et al. ................. 356/336 |
| 4,783,599 | 11/1988 | Borden . |
| 4,812,664 | 3/1989 | Borden . |
| 4,825,094 | 4/1989 | Borden et al. . |
| 4,990,795 | 2/1991 | Suzuki et al. .................... 356/339 |

FOREIGN PATENT DOCUMENTS

| | | |
|---|---|---|
| 0083633 | 4/1988 | Japan ............................... 356/336 |
| 0140044 | 6/1989 | Japan ............................... 356/336 |
| 0022534 | 1/1990 | Japan ............................... 356/338 |
| 0883714 | 11/1981 | U.S.S.R. . |
| 2016735A | 9/1979 | United Kingdom . |

OTHER PUBLICATIONS

"Benefits of Real-Time, In-Situ Particle Monitoring in Production Medium Current Implantation", Peter G. Borden and Lawrence A. Larson.

*Primary Examiner*—Richard A. Rosenberger
*Assistant Examiner*—Hoa Q. Pham
*Attorney, Agent, or Firm*—Haugen & Nikolai

[57] ABSTRACT

A vacuum particle detector includes a cavity providing a passage for fluid flow, a laser diode and beam shaping optics to form a substantially rectangular beam spanning the chamber. Light sensing optics, including a pair of biconvex lenses, receive light scattered when the particles suspended in the fluid intersect the beam. At least some of the scattered light is transmitted through the lenses to a photodetector. The photodetector width is selected in concert with the focal lengths of the biconvex lenses, to provide a viewing depth of field commensurate with the complete span of the beam across the chamber, whereby the photodetector responds to particles that intersect the beam over the entire span. A cone and a surrounding sleeve, both concentric about an axis of the beam, absorb the laser energy beam to provide an effective beam stop.

15 Claims, 4 Drawing Sheets

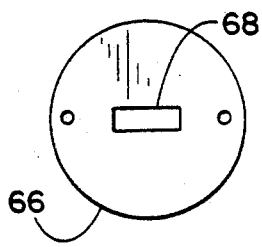
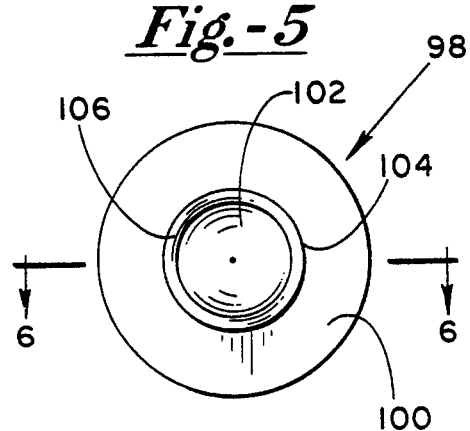
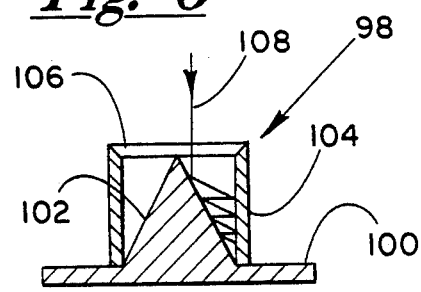
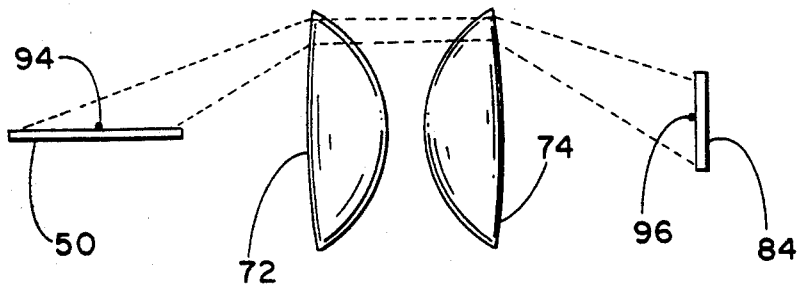

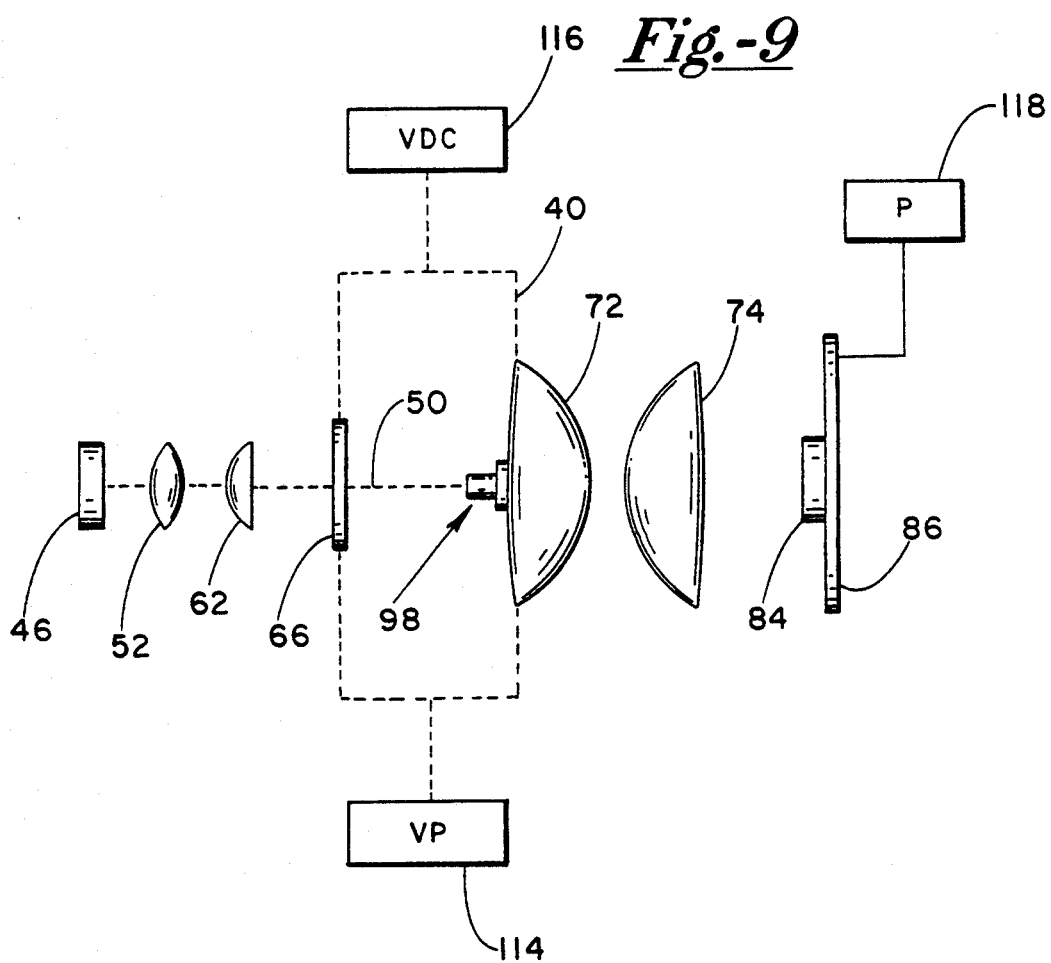

VACUUM PARTICLE DETECTOR

BACKGROUND OF THE INVENTION

The present invention relates to instruments for detecting small particles, and more particularly to devices that utilize light scattering in monitoring particle flux.

The need to control particulate contamination arises in a variety of environments, including hospital operating rooms, in the pharmaceutical industry and in aerospace manufacturing. The need arises in processing semiconductor wafers, where contamination by fine particles can substantially reduce yield.

In semiconductor chip fabrication, one well known method of monitoring particle contamination is to periodically insert test wafers into the process equipment, after which the test wafers are observed with a surface defect scanner or microscope, and the particles counted. This technique is labor intensive and does not provide continuous, real time monitoring of particulate contamination.

Another approach, disclosed in U.S. Pat. No. 4,783,599 (Borden), employs a flow of fluid through a pipe section or other volume defining structure, with a laser beam directed through a window into and across the pipe section, perpendicular to fluid flow through the section. The beam is focused near the center of the pipe section, and particles passing through the beam near the focal point scatter light. The scattered light is focused through a lens onto a detector, while light in the beam itself is blocked and thereby prevented from reaching the lens. The detected scattered light indicates the passage of a particle through the beam, and also can indicate the size of the particle. A problem with this arrangement is that the focal spot of the laser is small, generally less than a cubic millimeter. Thus, only a small fraction of the particles in fluid flow are detected.

The Borden patent further discloses a particle detector in which a collimated light beam is directed through a pipe section perpendicular to the direction of liquid flow through the pipe section, and into a beam stop tube. A pair of photodiodes, mounted to a window along the pipe section and located on opposite sides of the beam, respond to scattered light in a manner that detects particles but avoids mistaken identification of bubbles in the liquid as particles.

U.S. Pat. No. 4,825,094 (Borden et al) discloses a device for monitoring particle fallout in real time, including a laser source for generating a beam and a pair of spaced apart mirrors for reflecting the laser beam multiple times between the mirrors, then to a beam stop. A cylindrical tube, attached to the housing that mounts the laser and mirrors, surrounds an opening in the housing proximate the beam, to ensure that particle containing air is relatively still and virtually static near the reflected beam. The multiple reflections of the beam form a sheet or grid of light, whereby some particles in the flow intersect the sheet and scatter light.

In U.S. patent application Ser. No. 07/416,958 filed Oct. 4, 1989 and assigned to the assignee of the present application, a single particle detector employs opposed cylindrical mirrors and a flat mirror to define a sensing volume in which a laser beam is reflected multiple times between the mirrors to form a sheet of light. Single particles intersecting the sheet are measured based on light extinction. Light scattering, however, is preferred in connection with smaller particles, which may be insufficient in profile or in concentration to generate a reading based on extinction.

A light scattering photometer is disclosed in U.S. Pat. No. 4,178,103 (Wallace), in which liquid is formed into a curtain for particle detection. A laser beam is focused to provide a beam waist at the curtain. Direct beam energy is reflected away from the beam path by a radiant energy trap, while scattered light within a predetermined range of angles is admitted through a mask to a focusing lens, focused at a field stop wheel, diverged to another focusing lens and then focused at a detector.

While these detectors perform satisfactorily in their intended environments, there remains a need for a device that effectively monitors particle flux in a wide variety of manufacturing process environments.

Therefore, it is an object of the present invention to provide a particle sensing device usable in situ to continuously monitor particle flux in connection with a flow of fluid including a particulate suspension.

Another object of the invention is to provide a particle flux counting device employing light scattering, in which the viewing volume is substantially enlarged beyond a focal point or beam waist, without the need for multiple reflections of the beam.

A further object is to provide, in a particle monitoring device utilizing light scattering, an effective means for blocking the unscattered beam to prevent its reaching the sensing means employed to detect scattered light.

Yet another object is to provide a light scattering particle sensing device that is relatively inexpensive, yet effective in monitoring particle flux in fluids, over a wide range of fluid flow velocities.

SUMMARY OF THE INVENTION

To achieve these and other objects, there is provided an apparatus for detecting particles in a fluid stream. The apparatus includes a means forming a particle detection chamber having an inlet and an outlet at opposite ends thereof. The chamber is substantially uniform in transverse profile along its longitudinal length. A means is provided for drawing a fluid in a substantially non-turbulent flow longitudinally through the chamber from the inlet to the outlet. A means is provided for generating a beam of monochromatic energy and projecting the beam transversely in beam span across a transverse width of the chamber. A major profile of the beam is normal to the direction of the flow. A collecting means receives monochromatic energy scattered by particles suspended in the fluid as the particles intersect the beam along the transverse width. The collecting means includes converging optics substantially concentric on a beam axis of the beam and having first and second focal points and a predetermined focal length. Converging optics are mounted with respect to the beam to locate the first focal point along and at least approximately centered within the beam span. A photodetector means is positioned at least approximately at the second focal point and has a predetermined photodetector width corresponding to the predetermined focal length, to provide a depth of field encompassing substantially the entire beam span, whereby the photodetector receives light scattered by virtue of particles intersecting the beam substantially over the entire beam span. A beam stopping means is provided for substantially preventing radiant energy other than the scattered radiant energy from reaching the photodetecting means.

Preferably the collecting means includes two spaced apart convex aspherical lenses, each with a focal length at least 80 percent of the transverse width. This is longer than a corresponding focal length used in the conventional apparatus described above, where the viewing volume is restricted to the area immediately about the beam waist. The longer focal length increases the depth of field to the entire beam span as desired, without the need to increase the photodetector width. Thus, the increased depth of field does not increase susceptibility to noise.

A further feature of the invention is the larger diameter of the aspherical lenses as compared to the conventional approach, as well as the biconvex or bispherical lens construction. More particularly, the biconvex lenses have a diameter at least equal to the transverse width of the chamber. This feature enhances the angular range over which scattered light is collected and ultimately detected. The biconvex structure reduces distortion, particularly near the peripheries of the lenses, to enhance the transmission of scattered light.

The preferred beam stopping means includes a cylindrical cup mounted concentrically about the beam, and open at one end to receive the beam. A cone, centered within the cup, has an apex pointed at the beam, on the beam axis and recessed within the cup. The cup and cone are formed of blue anodized aluminum, which is particularly effective in absorbing monochromatic energy at the preferred wave length, i.e. in the far infrared range, more particularly 780 nanometers.

The laser beam preferably is generally rectangular along the beam span, having a width (perpendicular to the direction of fluid flow) substantially larger than its thickness in the direction of fluid flow. For example, the beam can be about 2.5 millimeters wide, with a thickness of 0.1 mm. The relatively large width insures that the beam span covers a fraction of the chamber profile sufficient for reliable particle monitoring. Conversely, the reduced thickness maintains the laser energy concentrated such that particles as small as about 0.2 microns in diameter scatter sufficient light to activate the photodetector as they intersect the beam span, even though they occupy the span only momentarily.

The conventional approach, of sensing only light scattered by particles intersecting the beam near the waist or focal point, has certain advantages not afforded by the much larger depth of field provided in accordance with the present invention. When only the beam waist or focal point is utilized, particles can be sized as well as detected, and optics can be tailored for expected conditions, such as an anticipated range of particle size and flow position. This provides single particle detection, rather than particle flux counting as in the present invention.

Nonetheless, devices constructed in accordance with the present invention have been found surprisingly effective in detecting particles as small as 0.2 microns in diameter, and can be used with fluids over a wide range in flow velocities, e.g. from about 20 to about 1200 liters per minute through a chamber of 50 millimeters in diameter. The result is a versatile device that can be employed to provide continuous, in situ monitoring of particle flux in a wide variety of manufacturing process environments.

IN THE DRAWINGS

For a better understanding of the above and other features and advantages, reference is made to the following detailed description and to the drawings, in which:

FIG. 4 is an elevational view of an aperture plate used in the detector;

FIG. 5 is an elevational view of a beam stop used in the detector;

FIG. 6 is a sectional view taken along the line 6—6 in FIG. 5;

FIG. 7 is a schematic view of a scattered light collecting assembly of the device;

FIG. 8 is a schematic representation of a laser energy beam generated by the device; and FIG. 9 is a schematic view illustrating utilization of the device as part of a particle flux monitoring system.

DETAILED DESCRIPTION OF THE PREFERRED EMBODIMENTS

Figure 1:
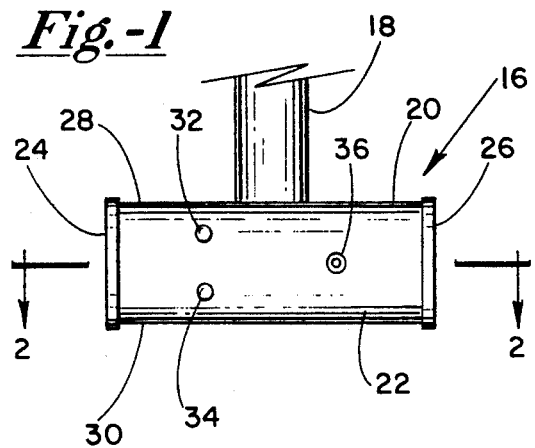
FIG. 1 is a front elevational view of a vacuum particle detector constructed according to the present invention.

Turning now to the drawings, there is shown in FIG. 1 a vacuum particle detector 16 and a cylindrical intake conduit 18 extended upwardly from the detector. Detector 16 has a rectangular housing 20 formed of aluminum or other suitable metal, including a front panel 22, side panels 24 and 26, top and bottom panels 28 and 30 and a back panel (not illustrated). Located on front panel 22 are an indicator light 32 actuated responsive to particle detection, and a status light 34 for indicating that a laser employed in the detector is functioning. A terminal suited for connection to a digital processor is also mounted to the front panel, as indicated at 36.

Figure 2:
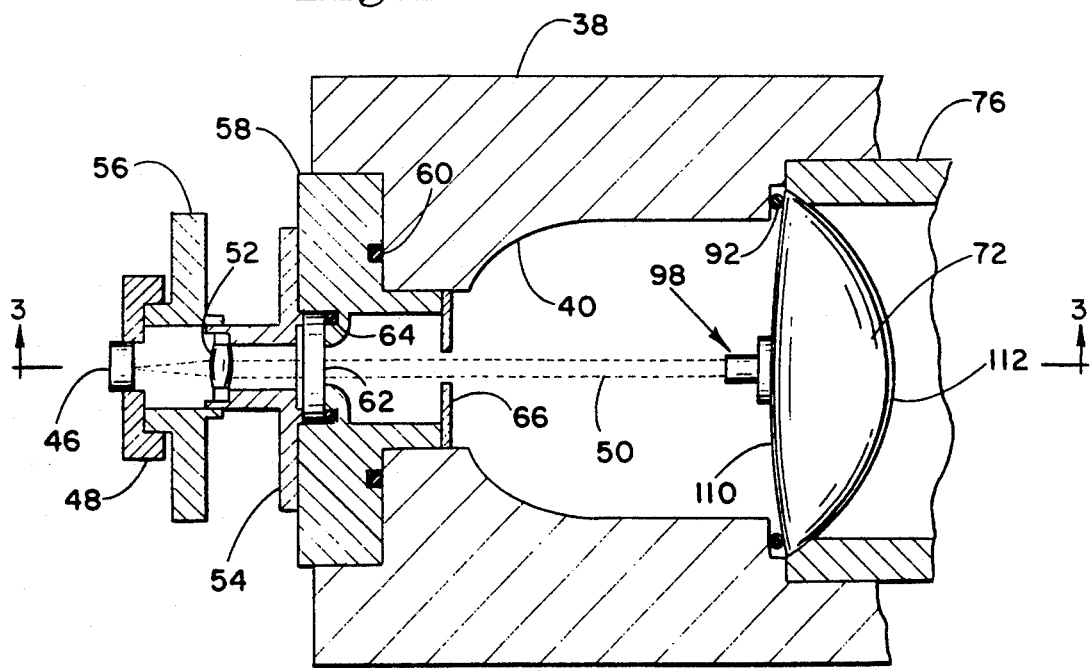
FIG. 2 is a top sectional view taken along the line 2—2 in FIG. 1.

Inside of housing 20 (FIGS. 2 and 3), a body 38 aluminum defines a chamber 40 extended through detector 16 from top inlet 42 to bottom exit 44. Chamber 40 is substantially uniform in horizontal profile along its vertical length, and is aligned with the interior of intake conduit 18. Chamber 40 has a somewhat U shaped profile as seen in FIG. 2. Chamber 40 and the interior of conduit 18 thus cooperate to define a passage that accommodates the flow of air or another fluid, vertically downward as viewed in FIG. 3. Intake conduit 18 tends to smooth the fluid flow and prevent undue turbulence in the chamber.

Detector 16 includes a means for generating a monochromatic energy beam, more particularly a laser diode 46 emitting energy in the far infrared range. An end cap 48 is employed to mount laser diode 46 with respect to the detector housing. Laser diode 46 is an AlGaAs laser emitting a laser beam 50 having a wave length of 780 nanometers.

A biaspheric collimating lens 52 is mounted within an annular support 54. An annular piece 56 connected to end cap 48 is adjustably positionable with respect to annular support 54 for fine adjustment of the horizontal distance between laser diode 46 and collimating lens 52.

An annular support 58 is secured to body 38, with a sealing ring 60 providing a fluid seal between support 58 and the body. A cylindrical lens 62 is mounted within annular support 58 through a sealing ring 64 to provide a fluid seal.

An aperture plate 66 (FIG. 4) is attached to the end of annular support 58 remote from the cylindrical lens. An aperture 68, approximately 3 millimeters wide (horizontal dimension) by 0.8 millimeters in height, is formed through the aperture plate. Plate 66 is constructed of stainless steel and given a dull black oxide finish.

Figure 3:
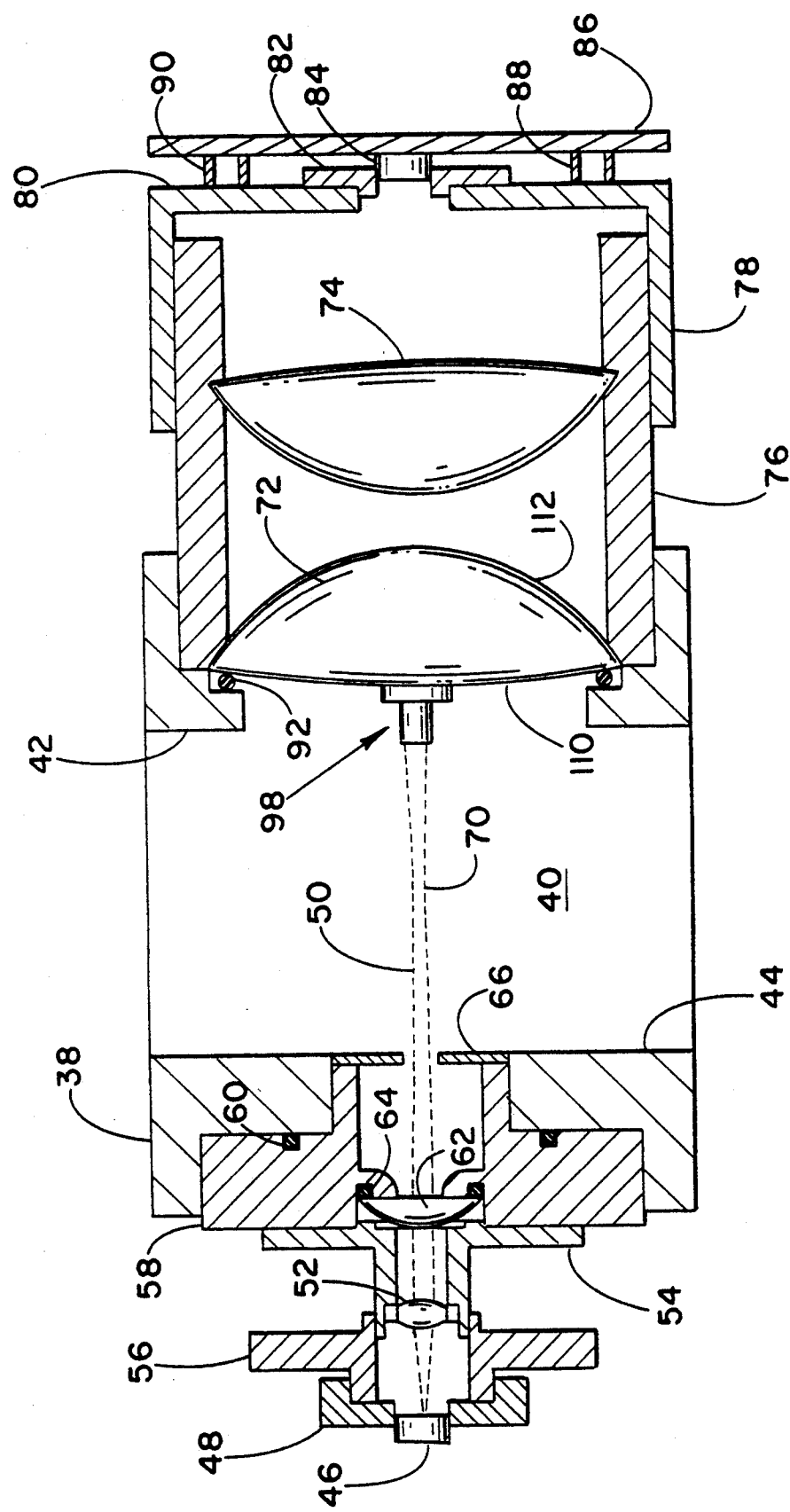
FIG. 3 is a side sectional view taken along the line 3—3 in FIG. 2.

Beam 50 when emitted from laser diode 46 is in the shape of a cone, diverging in the direction away from the laser diode or to the right as viewed in FIGS. 2 and 3. Collimating lens 52 converges beam 50 to give the beam a somewhat rectangular shape as it leaves the collimating lens. Cylindrical lens 62 further converges the beam, but only in the vertical direction, thus to impart to the beam a generally rectangular profile in which a horizontal width of the beam is substantially greater than a vertical beam thickness. Aperture plate 66 controls the beam in the sense of allowing into chamber 40 only the direct beam, on which aperture 68 is centered. In chamber 40, beam 50 continues to converge to a beam waist 70 near the center of the chamber, then diverges beyond the center. Beam 50 spans the entire horizontal width of chamber 40, and across the span has a width in the range of 2.2–3 millimeters, more preferably 2.5 millimeters. Given a width of 2.2 millimeters and a chamber diameter of about 50 millimeters, the surface area or profile of the beam in a horizontal plane provides a detection area of about 1.1 square centimeters, approximately 6 percent of the cross sectional area of chamber 40 taken in a horizontal plane.

Particle detector 16 further includes optics for receiving laser energy scattered by particles suspended in the fluid as the particles intersect beam 50. The optics include a pair of biconvex (more particularly, convex back aspheric) lenses 72 and 74 supported within an annular frame 76, axially spaced apart from one another and concentric on the axis of beam 50. Annular frame 76 is mounted to body 38. That a sealing ring 92 provides a fluid seal between biconvex lens 72 and chamber 50. Also mounted to frame 76 is an end cap 78 including an end wall 80 with a circular opening centered on the beam axis. A sleeve 82 is fit into the opening, and supports a photodetector 84. The photodetector is electrically coupled to circuitry on a printed circuit board 86 mounted to end wall 80 through supports 88 and 90. The circuitry, in turn, is electrically coupled to processor terminal 36, to facilitate an electrical coupling for transmitting electrical pulses generated responsive to light impinging upon photodetector 84, to a signal processor.

Lens 72 is mounted to locate a focal point 94 (FIG. 7) of the lens at about the center of chamber 50, coincident with waist 70 of the beam. Lens 74 is substantially identical in construction to lens 72, and has the same focal length. Lens 74 is positioned to locate its focal point 96 at the surface of photodetector 84.

The utility of photodetector 84 for sensing scattered light depends upon preventing unscattered light in beam 50 from reaching the photodetector. To this end, a beam stop 98 is mounted to lens 72 and positioned concentrically on the beam axis. As seen in FIGS. 5 and 6, beam stop 98 includes a flat back plate 100, a cone 102 converging in the direction away from back plate 100 toward the center of the chamber, and a sleeve 104 assembled to the back plate to form a cup. Sleeve 104 has a diameter of about five millimeters, and an inclined rim 106 of the sleeve further ensures capture of substantially all of the 2.5 millimeters wide beam. The back plate, cone and sleeve all are constructed of blue anodized aluminum, which is particularly well suited for absorbing infrared light including light of the preferred 780 nanometer wavelength. As indicated at 108, incoming light tends to strike cone 102. The non-absorbed portion of the light is reflected to the inside wall of sleeve 104, the yet non-absorbed portion reflected back to the cone, and so on until substantially all of the energy is absorbed as heat by the beam stop.

As previously mentioned, biconvex lenses 72 and 74 are positioned to locate their respective focal points at the waist of the beam 50 and the surface of photodetector 84, respectively. Thus, light scattered by virtue of particles intersecting the beam waist reaches lens 72, is transmitted to lens 74 and reimaged upon photodetector 84 to trigger a response by the photodetector. However, in accordance with the present invention, light scattered by virtue of particles intersecting the beam over virtually the entire span from aperture plate 66 to beam stop 98 also is sensed by the photodetector. The focal length of lenses 72 and 74, their diameter, the biconvex structure of the lenses and the width (vertical dimension as seen in FIG. 3) of photodetector 84 all play a role in facilitating photodetector response to particles intersecting beam 50 remote from the beam waist.

More particularly, each of lenses 72 and 74 has a focal length of about 42 millimeters, as compared to a 37 millimeter focal length employed in connection with responding only to particles near the beam waist. This requires increased distance between beam waist 70 and photodetector 84, but increases the depth of field for a photodetector of a given width. As illustrated schematically in FIG. 7, a depth of field about focal point 94 corresponds to opposite edge regions of photodetector 84. Given the 42 millimeter focal length, the photodetector width corresponds to a depth of field that encompasses the entire span of beam 50 across chamber 40.

Further, the size of lenses 72 and 74 is substantially increased as compared to similar lenses in a conventional, more tightly focused arrangement, by a factor of at least one-and-one-half times the lens surface area. The increased surface area provides a wider range of angles at which scattered light is received by lens 72 and eventually transmitted to photodetector 84.

Another factor is the bispherical or biconvex construction of the lenses, for example as indicated at respective gradually curved and more severely curved profiles 110 and 112 of lens 72. Because both surfaces are convex, the curvature of each surface is less severe, reducing distortion and enhancing transmission of laser energy throughout the peripheral regions of lenses 72 and 74.

As mentioned above, the focal length of the lenses and the width of the photodetector are selected to provide a depth of field covering substantially the entire width of chamber 50. More particularly, the depth of field is increased by virtue of increasing the focal length rather than just the photodetector width. Although either could be increased to achieve a greater depth of field, increasing the focal length is preferred, since a relatively narrow photodetector is less susceptible to noise.

Thus, a feature of the present invention is that detector 16 responds to light scattering due to particles that intersect beam 50, not only in the region of beam waist 70 but throughout the beam span. As is apparent in FIG. 8, beam 50 is substantially narrower at waist 70 than it is near the periphery of chamber 40. As a result, the time averaged intensity of scattered light depends not only on the profile of a particle intersecting beam 50, but also upon the point of intersection and velocity. A particle intersecting beam 50 at the waist scatters light of greater intensity than the same particle intersecting the beam near the chamber periphery. Accordingly, detector 16 is not as effective a particle sizing device as compared to a conventional, narrowly focused device. Nonetheless, laser energy is sufficiently concentrated such that the entire horizontal profile of the beam is available for particle detection, as opposed to merely the region of the beam waist. Accordingly, in connection with manufacturing processes in which monitoring particle flux is of primary concern, and in which particle sizing is secondary, detector 16 provides an effective approach at substantially reduced cost.

Operation of detector 16 in a manufacturing environment is illustrated schematically in FIG. 9, where a pump 114 is employed to draw air in a flow through intake conduit 18 and chamber 40, then out of detector 16 through the bottom panel. As an example of a process environment, pump 114 draws down a vacuum deposition chamber 116 to a predetermined vacuum. Beam 50 is emitted from laser diode 46, collimated in lens 52 and projected through cylindrical lens 62. The beam then passes through aperture 68 into chamber 50, where it converges to waist 70, then diverges as it enters beam stop 98. Particles intersecting the beam scatter the laser energy, some of which reaches lens 72, for transmittal to lens 74 and convergence onto photodetector 84. In response to receiving the scattered light, photodetector 84 generates electrical pulses and provides the pulses to circuitry in printed circuit board 86. The signals are amplified and transmitted to a processor 118, where the signal is digitized and analyzed in a known manner to produce a continuous particle flux count based on continuous, in situ particle detection.

What is claimed is:

1. An apparatus for detecting particles in a fluid stream, including:
   a means forming a particle detection chamber having an inlet and an exit at opposite ends thereof, a length in a longitudinal direction and a width in a transverse direction substantially normal to the longitudinal direction, for accommodating a fluid in a substantially non-turbulent flow in the longitudinal direction through the chamber from the inlet to the outlet;
   a means for generating a beam of radiant energy and projecting the beam in the transverse direction in a beam span across the width of the chamber, with a major profile of the beam being normal to the longitudinal direction;
   a collecting means for receiving a portion of the radiant energy scattered by particles suspended in the fluid as the particles intersect the beam along said transverse width, including coverging optics substantially concentric on the beam and having first and second focal points and a predetermined focal length, said converging optics mounted with respect to the beam to locate the first focal point along and at least approximately centered within the beam span; a photodetector means positioned at least approximately at the second focal point and having a predetermined photodetector width corresponding to said predetermined focal length to provide a depth of field encompassing substantially the entire width of the chamber whereby the photodetector received light scattered by virtue of particles intersecting the beam substantially over the entire span; and
   a beam stopping means for substantially preventing radiant energy other than the scattered radiant energy from reaching the photodetecting means.

2. The apparatus of claim 1 wherein:
said predetermined focal length is at least 80 percent of said transverse width.

3. The apparatus of claim 1 wherein:
the collecting means includes two spaced apart convex aspherical lenses, each having a focal length at least 80 percent of said transverse width.

4. The apparatus of claim 3 wherein:
each of said lenses has a diameter at least equal to said transverse width.

5. The apparatus of claim 4 wherein:
each of the lenses is biconvex.

6. The apparatus of claim 1 wherein:
said beam stopping means includes a cylinder mounted concentrically about the beam at an end of the beam span remote from the beam generating means, and a cone centered within a cylinder with its apex pointed at the beam generating means.

7. The apparatus of claim 6 wherein:
said radiant energy is monochromatic, and said cylinder and cone are formed of blue anodized aluminum.

8. The apparatus of claim 1 further including:
a flow smoothing means upstream of the inlet for facilitating non-turbulent flow through the chamber.

9. The apparatus of claim 1 further including:
a means for drawing fluid through the chamber.

10. A process for detecting particles suspended in a fluid stream, including the steps of:
providing a fluid stream through a fluid passage, said fluid containing a suspension of particles;
projecting a radiant energy beam across a width of the passage in a beam direction perpendicular to the direction of fluid flow, and shaping the beam to provide a beam width perpendicular to the beam direction and the direction of flow, and a beam thickness parallel to the direction of flow, said beam width being substantially greater than the thickness;
collecting light scattered due to particles in the fluid stream intersecting the radiant energy beam at any point over substantially all of said passage width, by positioning converging optics to locate a first focal point of the converging optics along the beam and along the passage width; and
directing the scattered and collected light onto a photodetecting means substantially at a second focal point of said converging optics to generate an electrical signal corresponding to the intensity of the light so directed.

11. The process of claim 10 including the further step of:
preventing the radiant energy beam from reaching the photodetector.

12. The process of claim 11 wherein:
the step of preventing the radiant energy beam from reaching the photodetector includes collecting the beam and absorbing the radiant energy.

13. The process of claim 10 wherein:
said converging optics includes at least one biconvex lens, and said step of collecting scattered light includes aligning said at least one biconvex lens coaxially with the radiant energy beam, and positioning the at least one lens with respect to the passage to provide a depth of field substantially equal to the passage width.

14. The process of claim 10 wherein:
the step of providing a fluid stream includes drawing the fluid through the fluid passage using a vacuum pump.

15. The process of claim 10 including the further step of:
providing a smoothing means in the fluid passage upstream of the radiant energy beam, to insure against turbulent flow in the fluid stream.

* * * * *